United States Patent
Hayes et al.

(10) Patent No.: US 10,548,489 B2
(45) Date of Patent: Feb. 4, 2020

(54) FIBER BRAGG GRATING MULTI-POINT PRESSURE SENSING GUIDEWIRE WITH BIREFRINGENT COMPONENT

(71) Applicant: LAKE REGION MEDICAL, INC., Chaska, MN (US)

(72) Inventors: John Hayes, Cork (IE); Matheus Maria van Leest, Alkmaar (NL); Michael Benjamin Haverdings, Velserbroek (NL)

(73) Assignee: Lake Region Medical, Inc., Chaska, MN (US)

( * ) Notice: Subject to any disclaimer, the term of this patent is extended or adjusted under 35 U.S.C. 154(b) by 25 days.

(21) Appl. No.: 15/129,432

(22) PCT Filed: Oct. 30, 2015

(86) PCT No.: PCT/US2015/058434
§ 371 (c)(1),
(2) Date: Sep. 27, 2016

(87) PCT Pub. No.: WO2016/070110
PCT Pub. Date: May 6, 2016

(65) Prior Publication Data
US 2017/0238821 A1    Aug. 24, 2017

Related U.S. Application Data

(60) Provisional application No. 62/073,216, filed on Oct. 31, 2014, provisional application No. 62/073,203, filed on Oct. 31, 2014.

(51) Int. Cl.
*A61B 5/0215*    (2006.01)
*A61B 5/00*    (2006.01)

(52) U.S. Cl.
CPC ........ *A61B 5/02154* (2013.01); *A61B 5/6851* (2013.01); *A61B 2562/0247* (2013.01)

(58) Field of Classification Search
CPC .............. A61B 5/02154; A61B 5/6851; A61B 5/02007; A61B 5/0215; A61B 2562/0247;
(Continued)

(56) References Cited

U.S. PATENT DOCUMENTS

| | | |
|---|---|---|
| 35,648 A | 6/1862 | Dyer |
| 4,941,473 A | 7/1990 | Tenerz et al. |

(Continued)

FOREIGN PATENT DOCUMENTS

| | | |
|---|---|---|
| JP | 60260010 | 12/1985 |
| WO | 2003100488 | 12/2003 |

OTHER PUBLICATIONS

Jan. 22, 2016 PCT Search Report (Serial No. PCT/US15/58434)—Our Matter 5376.
(Continued)

*Primary Examiner* — Rex R Holmes
(74) *Attorney, Agent, or Firm* — Michael F. Scalise

(57) ABSTRACT

A system and method are presented for detecting and measuring pressure within a region of a body lumen or vessel. The pressure sensing system includes a light source for transmitting light through a pathway of polarization maintaining fiber optic wire. A distal portion of the polarization maintaining fiber optic wire is engaged to and extends along a guidewire. The distal portion of the fiber optic wire includes pressure sensing station(s) made up of fiber Bragg gratings (FBG). The light transmitted to and reflected from the FBGs on the two polarization modes of the polarization maintaining fiber optic wire can be analyzed to provide one or more pressure values.

19 Claims, 11 Drawing Sheets

(58) Field of Classification Search
CPC .. A61B 2562/0266; G01L 11/025; G02B 6/40
See application file for complete search history.

(56) References Cited

U.S. PATENT DOCUMENTS

| | | | |
|---|---|---|---|
| 5,005,584 A | 4/1991 | Little | |
| 5,125,058 A | 6/1992 | Tenerz et al. | |
| 5,313,957 A | 5/1994 | Little | |
| 5,452,393 A | 9/1995 | Stowe et al. | |
| 5,841,131 A * | 11/1998 | Schroeder | G01D 3/036 250/227.17 |
| 6,144,788 A | 11/2000 | Ang et al. | |
| 7,245,789 B2 | 7/2007 | Bates et al. | |
| 7,946,997 B2 | 5/2011 | Hubinette et al. | |
| 8,075,478 B2 | 12/2011 | Campos | |
| 8,391,652 B2 | 3/2013 | Bates et al. | |
| 8,560,048 B2 | 10/2013 | Eberle et al. | |
| 8,989,528 B2 | 3/2015 | Udd | |
| 9,078,561 B2 | 7/2015 | Eberle et al. | |
| 2002/0041723 A1 | 4/2002 | Ronnekleiv et al. | |
| 2003/0169972 A1 * | 9/2003 | Stanton | G02B 6/04 385/54 |
| 2007/0116408 A1 * | 5/2007 | Eberle | A61B 1/00165 385/31 |
| 2008/0281209 A1 | 11/2008 | Arkwright et al. | |
| 2009/0059727 A1 | 3/2009 | Bates et al. | |
| 2009/0190892 A1 * | 7/2009 | Kamins | G02B 6/241 385/121 |
| 2009/0208173 A1 * | 8/2009 | Schumann | G02B 6/40 385/77 |
| 2009/0262361 A1 * | 10/2009 | Tanioka | A61B 5/0066 356/479 |
| 2010/0014810 A1 | 1/2010 | Eberle et al. | |
| 2010/0080510 A1 * | 4/2010 | Riska | G02B 6/255 385/54 |
| 2010/0087732 A1 | 4/2010 | Eberle et al. | |
| 2010/0113942 A1 | 5/2010 | Eberle | |
| 2010/0135111 A1 | 6/2010 | Bates et al. | |
| 2011/0022026 A1 | 3/2011 | Fleischhacker et al. | |
| 2011/0071608 A1 | 3/2011 | Fleischhacker et al. | |
| 2011/0123154 A1 | 5/2011 | Eberle et al. | |
| 2012/0051697 A1 * | 3/2012 | Kadar-Kallen | G02B 6/3885 385/78 |
| 2012/0108943 A1 | 5/2012 | Bates et al. | |
| 2012/0197097 A1 | 8/2012 | Chan et al. | |
| 2012/0271339 A1 | 10/2012 | O'beirne et al. | |
| 2013/0148933 A1 | 6/2013 | Eberle et al. | |
| 2013/0218032 A1 | 8/2013 | Belleville | |
| 2013/0317372 A1 * | 11/2013 | Eberle | A61B 5/02154 600/478 |
| 2013/0317485 A1 | 11/2013 | Lupton | |
| 2014/0010500 A1 * | 1/2014 | Saito | G02B 6/3885 385/70 |
| 2014/0180030 A1 | 6/2014 | Dorando | |
| 2014/0180032 A1 * | 6/2014 | Millett | A61B 5/02007 600/301 |
| 2014/0241385 A1 * | 8/2014 | Fomin | G02B 6/4296 372/6 |
| 2014/0308010 A1 * | 10/2014 | Mougin | G02B 6/3825 385/76 |
| 2014/0350414 A1 * | 11/2014 | McGowan | A61B 5/02154 600/480 |
| 2014/0363126 A1 | 12/2014 | Kat | |
| 2015/0032027 A1 | 1/2015 | Lupton | |
| 2015/0055913 A1 * | 2/2015 | Imoto | C03B 19/00 385/24 |
| 2015/0205126 A1 * | 7/2015 | Schowengerdt | G06T 13/40 345/633 |
| 2015/0241614 A1 * | 8/2015 | Ide | G02B 6/00 359/204.4 |
| 2015/0331192 A1 * | 11/2015 | Hall | G02B 6/3885 385/24 |
| 2016/0020573 A1 * | 1/2016 | Watanabe | G02B 6/2856 359/341.3 |
| 2016/0041354 A1 * | 2/2016 | Guenter | G02B 6/4432 385/86 |
| 2016/0139336 A1 * | 5/2016 | Bansal | G02B 6/2551 385/96 |
| 2016/0328884 A1 * | 11/2016 | Schowengerdt | G02B 6/32 |
| 2017/0031111 A1 * | 2/2017 | Fujiwara | G02B 6/40 |

OTHER PUBLICATIONS

Byeong Ha Lee, el al., "Interferometric Fiber Optic Sensors," Sensors, vol. 12, pp. 2467-2486, Feb. 23, 2012.

Jan. 21, 2016 PCT Search Report (Serial No. PCT/US15/58408)—Our Matter 5387.

Extented European Search Report, Application No. 15853841.3, dated Jun. 18, 2018.

Frazao, et al., "Simultaneous measurement of multiparameters using a Sagnac interferometer with polarization maintaining side-hole fiber", Applied Optics, vol. 47, No. 27, Sep. 20, 2008, pp. 4841-4848.

Alan D. Kersey, "A Review of Recent Developments in Fiber Optic Sensor Technology", Optical Fiber Technology 2, 291-317, Article No. 0036. Fiber Optic Smart Structures Section, Naval Research Laboratory, Washington, DC 20375-5000, Feb. 13, 1996.

* cited by examiner

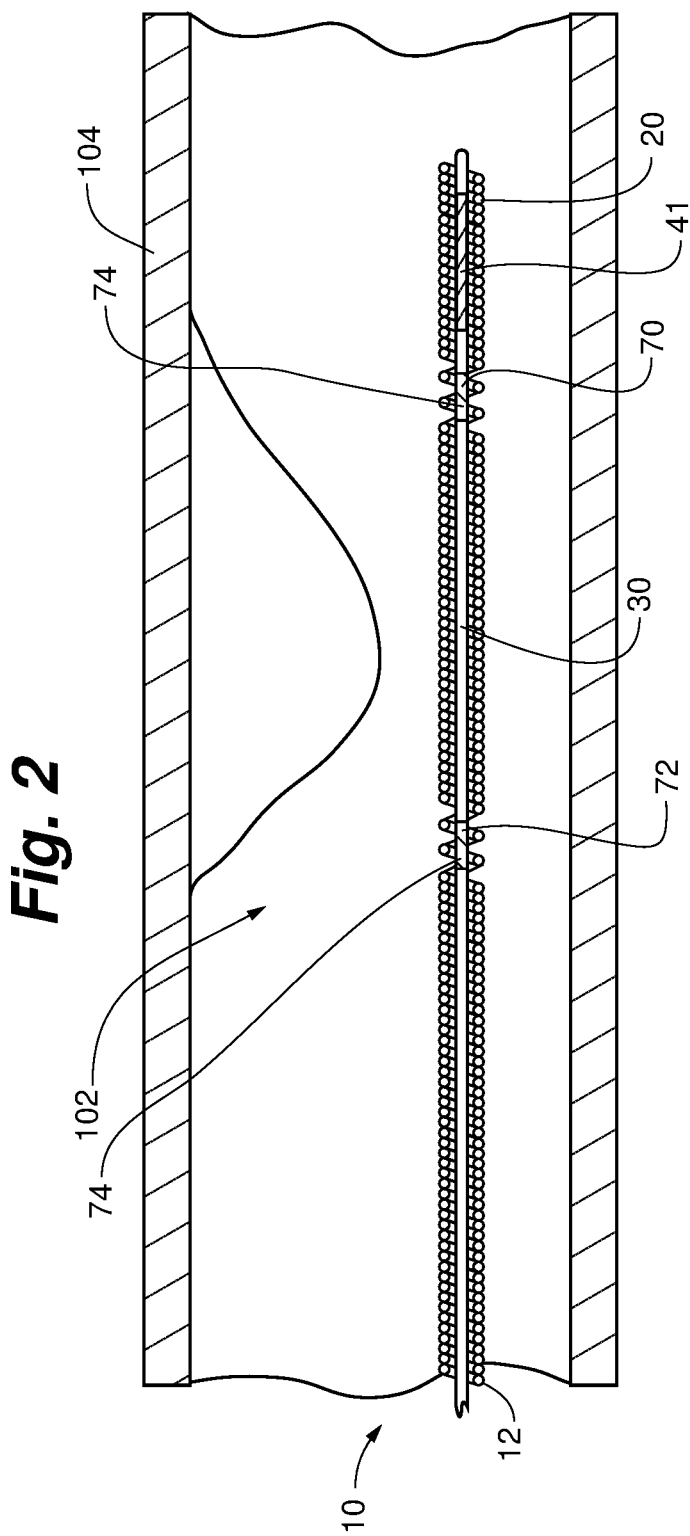

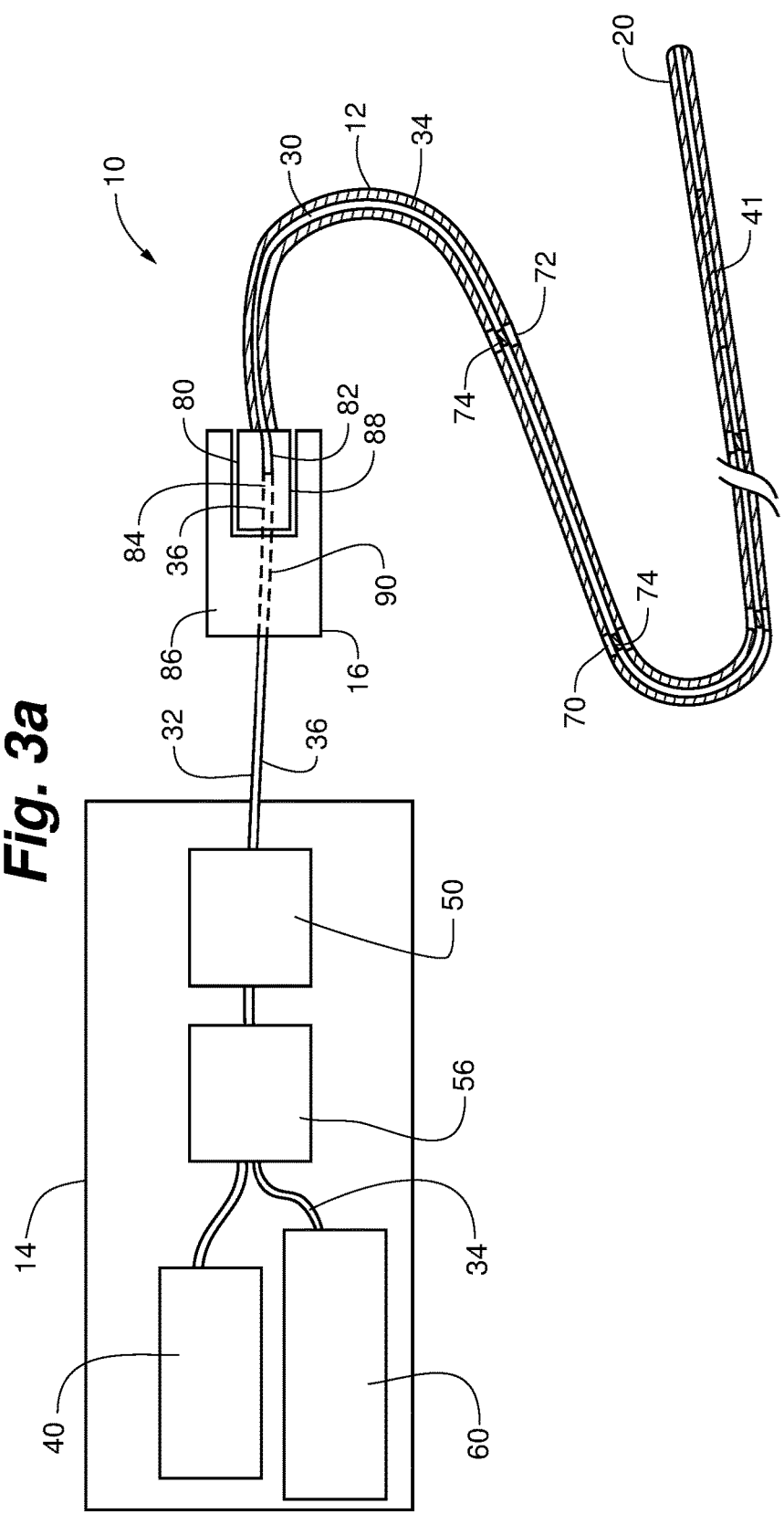

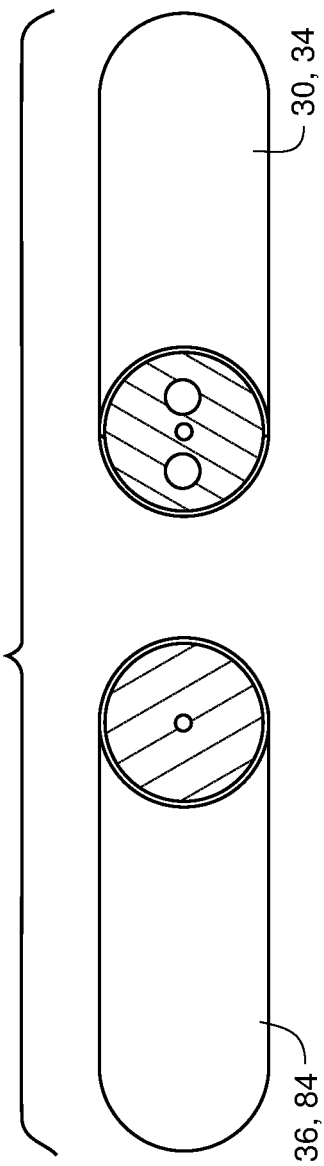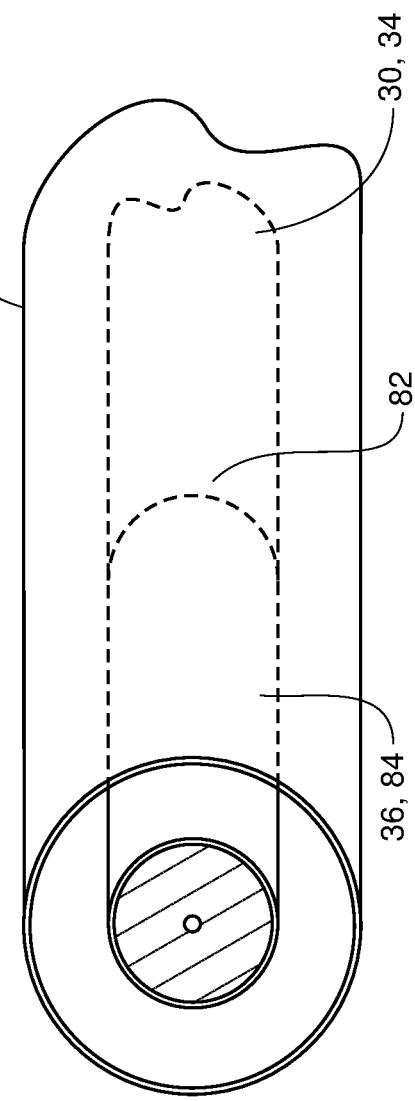

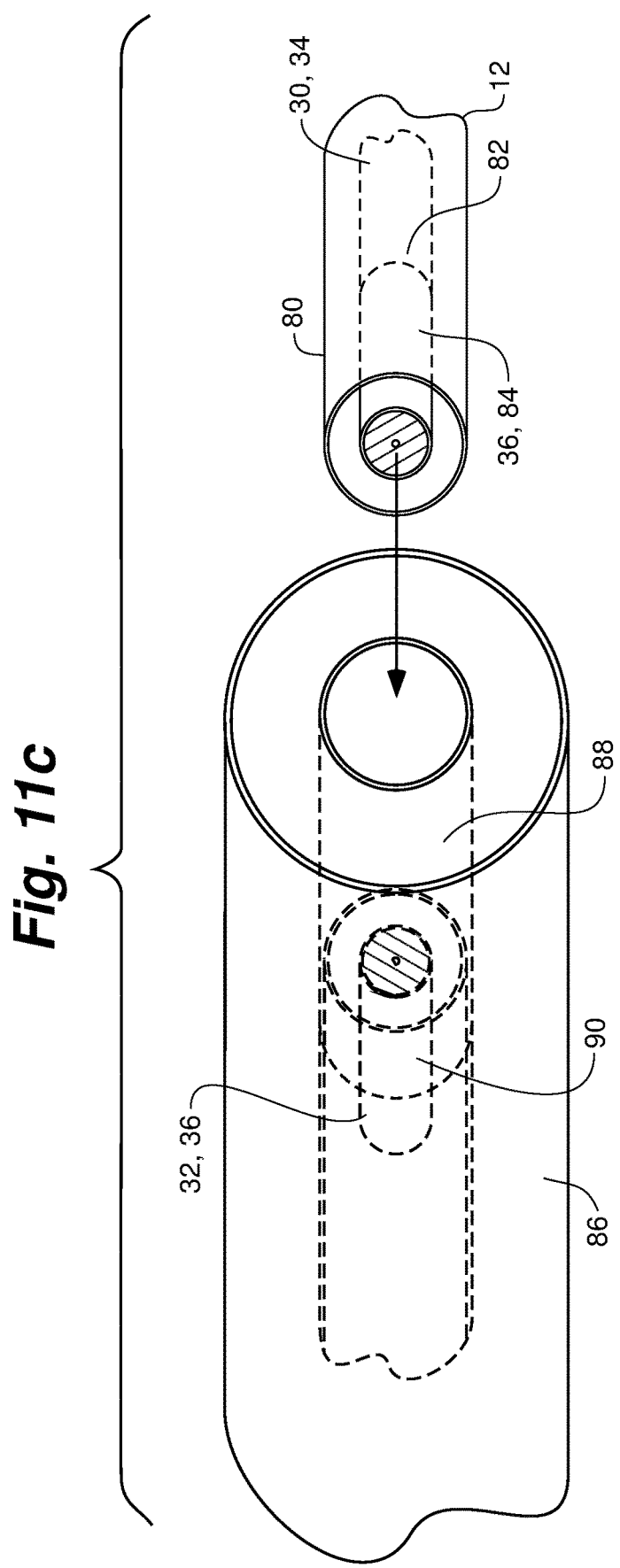

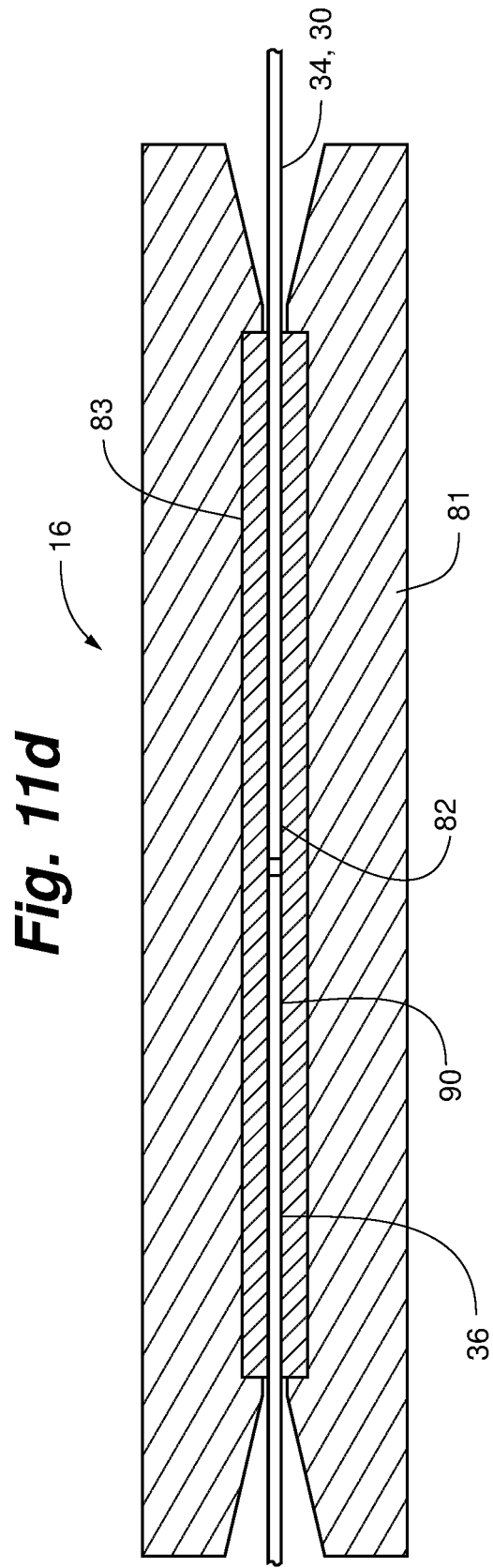

FIBER BRAGG GRATING MULTI-POINT PRESSURE SENSING GUIDEWIRE WITH BIREFRINGENT COMPONENT

CROSS-REFERENCE TO RELATED APPLICATIONS

This application is a utility filing claiming priority to provisional filings 62/073,216 and 62/073,203, both of which were filed on Oct. 31, 2014. The entire contents of the 62/073,216 and 62/073,203 provisional applications are incorporated herein by reference.

FIELD OF THE INVENTION

This disclosure relates to the field of medical devices, and specifically to catheter systems including guidewires for use in the collection of diagnostic information, such as for example pressure, from multiple sites within a body lumen.

SUMMARY

A known technique of comparing pressures on either side of an occlusion or other affected area of a vessel to determine if additional treatment is necessary is known as Fractional Flow Reserve (FFR). Examples of devices and methods used in FFR measurement procedures are shown and described in U.S. Pat. Nos. 5,987,995 and 6,868,736, the entire content of each of which being incorporated herein by reference.

Embodiments of the present disclosure include catheter systems, and particularly those that include a diagnostic guidewire assembly equipped with one or more pressure sensors that can be placed across a lesion, occlusion or other affected area within a vessel and then near-simultaneously detect pressures on either side of the affected area.

The diagnostic guidewire assembly and system of the present disclosure provides a benefit over known FFR systems in that upstream and downstream pressures are detected simultaneously, with a distal region of the guidewire assembly positioned across the occlusion or affected region. With the guidewire assembly in place, the detected pressures are analyzed, and depending on their values, a determination of whether further treatment of the affected area is required occurs without removal of the guidewire. If it is determined that further treatment (such as balloon angioplasty, stent delivery, etc.) is required, the diagnostic guidewire assembly remains in place to guide the subsequent treatment system (POBA catheter, stent delivery catheter, etc.) to the affected area. In addition, following the therapeutic treatment, the guidewire assembly can remain in place to conduct a follow-up simultaneous FFR diagnosis procedure to determine the efficacy of the therapeutic treatment. This process may be repeated as needed, with the guidewire assembly remaining in place throughout the one or more diagnostic and therapeutic procedures.

The ability to conduct such improved simultaneous FFR diagnosis with the same guidewire that can be used to advance the treatment catheter to the affected site of the vessel is not only more efficient than multiple-wire systems, it also minimizes irritation to the vessel and reduces the risk of embolization.

Stenting and angioplasty devices and procedures are well known and understood by those of skill in the art. A description of such procedures and example devices may be found in U.S. Pat. No. 4,886,062, the entire content of which is incorporated herein by reference.

Embodiments of the aforementioned diagnostic guidewire system can utilize a variety of sensors and sensory techniques to detect pressure values. In at least one embodiment the guidewire is equipped with a fiber optic wire. At a distal region of the fiber optic wire are a plurality of pressure sensors. Each pressure sensor is comprised of at least one fiber Bragg grating (FBG), with each FBG having a distinct grating period to provide correspondingly distinct peak reflection wavelengths of reflected light through the fiber optic wire. Precise monitoring of the spectral peak position of the light returned from each FBG is analyzed and compared, via an interrogator (light receiver), to provide a pressure difference between the upstream and downstream values.

In one embodiment, the fiber optic wire is a polarization-maintaining (PM) fiber optic wire. Polarization maintaining fiber optic wires maintain the polarization of light within the fiber during propagation. Polarization-maintaining fibers typically introduce birefringence into the fibers so that two polarization modes exist and propagate within the fiber having different refractive indexes and different light velocities. When combined with a FBG, the differing refractive indexes supporting both polarization modes in the PM fiber result in the FBG reflecting different wavelengths of light in the two different polarization modes. While various types of PM fiber may be used, twin-hole PM fiber provides unique pressure sensitive characteristics when compared to other types of PM fiber. The refractive indexes of the two polarization modes in twin-hole fiber optic wire change differently when subjected to external pressure, which means that variations in the two wavelengths reflected by the FBG in the twin-hole PM fiber can be used to measure the external pressure at the FBG.

Examples of a systems using FBGs and an interrogator system for analyzing reflected light is described in U.S. Publication 2014/0363126, to P. L. Kat and filed Jun. 5, 2014, and U.S. Pat. No. 8,345,238; the entire content of each being incorporated herein by reference.

These and other embodiments of the invention are disclosed herein and are illustrated in for following drawings.

BRIEF DESCRIPTION OF THE DRAWINGS

FIG. 2 is a detailed view of the distal end region of the guidewire system shown in FIG. 1 positioned across a lesion site within a body vessel.

FIG. 3a is a schematic isolated view of the guidewire system shown in FIG. 1.

FIG. 3b is a detailed view of the distal tip of the guidewire assembly shown in FIG. 3a.

FIG. 4b is a cross-sectional view of the guidewire assembly shown in FIG. 4a.

FIG. 5b is a cross-sectional view of the guidewire assembly shown in FIG. 5a.

FIG. 6b is a cross-sectional view of the guidewire assembly shown in FIG. 6a.

FIG. 7b is a cross-sectional view of the guidewire assembly shown in FIG. 7a.

FIG. 11a-11d is a series of images depicting the elements of the connector shown in FIGS. 1 and 3.

DETAILED DESCRIPTION

Figure 1:
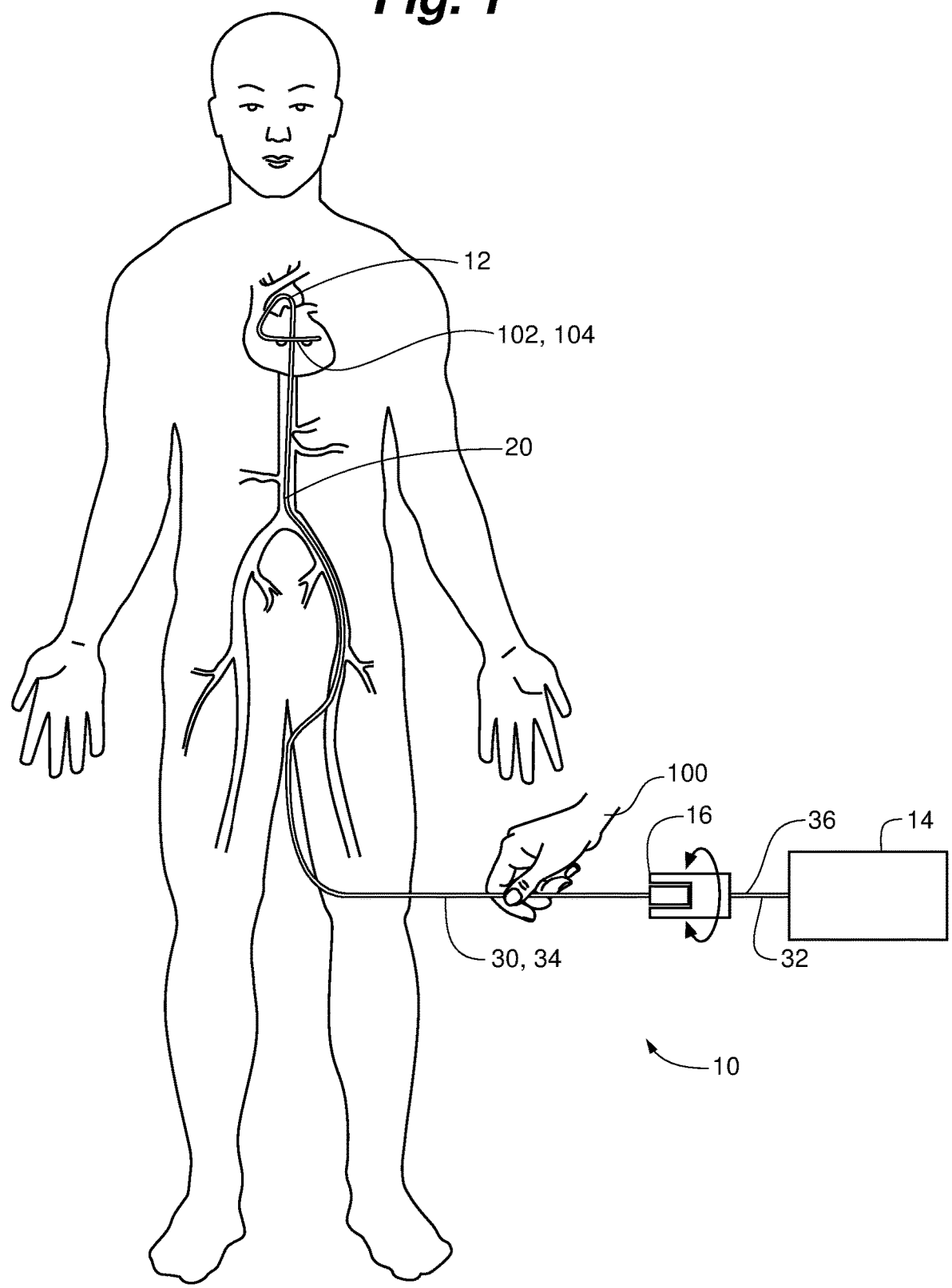
FIG. 1 is a schematic view of a guidewire system in its environment of use.

In the embodiments described herein, and shown in the various FIGS. 1-13, the system 10 can be viewed as being comprised of three primary elements or assemblies in the following manner:

A distal or guidewire assembly 12 of the system 10 is comprised primarily of a guidewire 20 and a distal fiber optic wire 30, as well as associated elements described in greater detail below.

A proximal assembly 14 of the system 10 is comprised of a proximal fiber optic wire or pathway of fibers 32, a light source 40, a polarization control unit 50, a reflected light receiver 60 as well as other components for sending and analyzing light signal(s) transmitted through the fiber optic wires 30 and 32, such as is seen in FIG. 3.

Connecting the distal guidewire assembly 12 and the proximal assembly 14 is a connection assembly or connector 16 which connects the distal fiber optic wire 30 and proximal fiber optic wire 32. Embodiments of the system 10 shown with assemblies 12, 14 connected by connector 16 are depicted in FIGS. 1, 3 and 12-13.

In FIG. 1 a schematic view is provided, which illustrates an example use of the system 10 in a diagnostic FFR procedure. In such a procedure the guidewire assembly 12, enters the patient via Seldinger or other technique, and is introduced into the vasculature. Under fluoroscopy or other imaging techniques, the guidewire assembly 12 is advanced by the physician or practitioner (represented by the depicted hand) 100 to an affected region 102 of a vessel 104, such as is shown in FIG. 2. The affected region 102 may be a lesion, occlusion or other abnormality within the vessel 104 causing restriction in blood flow therethrough.

The guidewire assembly 12 may have a variety of configurations, some examples of which are illustrated in FIGS. 4a-7b. Common to all configurations is the presence of a guidewire 20 having a guidewire body or shaft 22, which supports the distal fiber optic wire 30.

The distal fiber optic wire 30 includes one or more sensor stations, such as stations 70 and 72 shown. Each sensor station 70, 72 is comprised of a Fiber Bragg Grating (FBG) 74 within the core of the distal fiber optic wire 30. While the use and function of the FBG 74 and sensor stations 70,72 are discussed in greater detail below, it should be noted that in the various embodiments shown and described herein a key feature of the present invention is to configure the guidewire assembly 12 in such a manner that at least those regions of the fiber optic wire 30 which include FBGs 74 are directly exposed to the vascular environment. That is to say: the region or regions of the fiber optic wire 30 which include a sensor station is directly exposed to the interior of the vessel without any additional membranes (the optical wire 30 and/or the guidewire 20 are membrane-free), sleeves or other structures interposed between the sensor station and the vessel environment. In this manner, environmental conditions of the vessel (such as blood pressure) directly affects the sensor station without interference or enhancement by intervening structure.

The examples of the guidewire assembly 12 shown in FIGS. 4a-7b illustrate some types of possible configurations that provide the preferred FBG exposure.

Figure 4A:
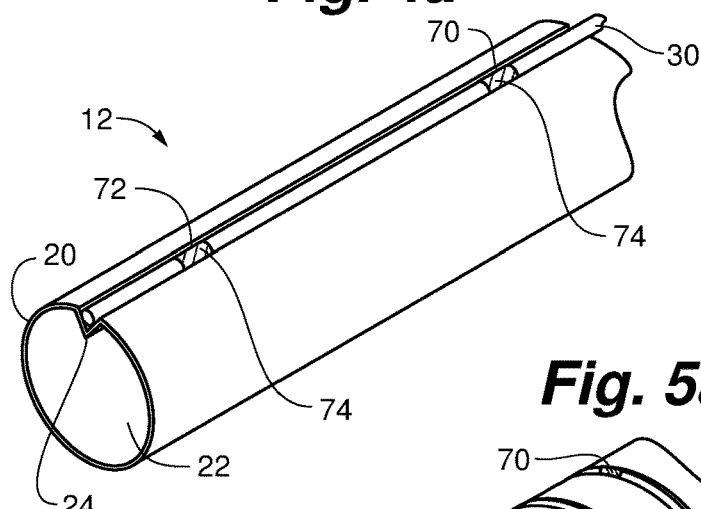
FIG. 4a is a perspective view of an embodiment of a distal region of the guidewire assembly shown in FIG. 3.
Figure 4B:
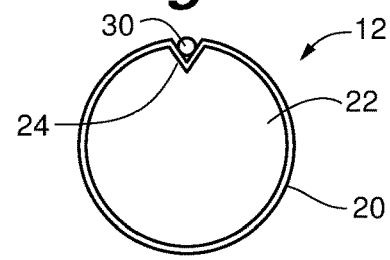

In FIGS. 4a and 4b the guidewire shaft 22 defines a linear groove or channel 24. The distal fiber optic wire 30 is positioned at least partially within and extends along the channel 24. This configuration provides protection to the fiber optic wire 30 yet still allows the FBGs 74 of the sensor stations 70 and 72 to remain exposed through the channel opening 26. In this configuration, the upper surface of the FBGs are exposed to the interior of the vessel, while the lower surface of the FBGs abuts the channel 24.

Figure 5A:
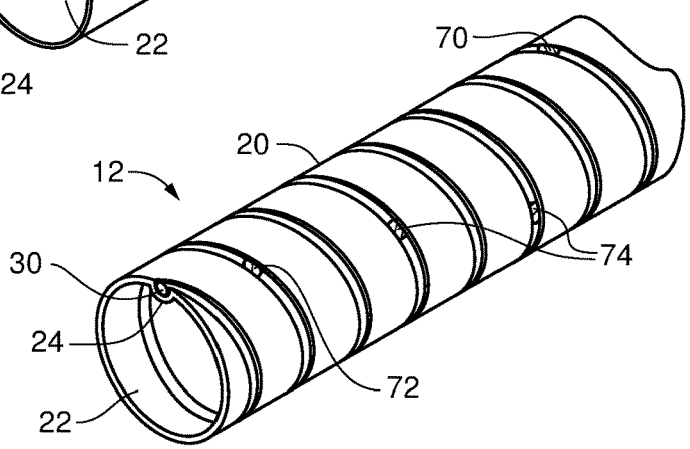
FIG. 5a is a perspective view of an embodiment of a distal end region of the guidewire assembly shown in FIG. 3.
Figure 5B:
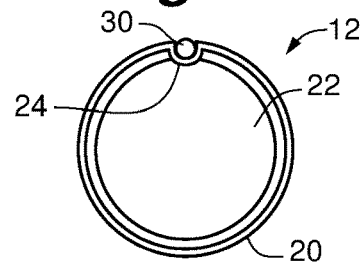

In FIGS. 5a and 5b an alternative configuration is shown wherein the channel 24 is a helical groove. The helical grove provides similar protection to the fiber optic wire 30 and also allows the sensors 70 and 72 to be displaced around the circumference of the guidewire 20 in order to provide a 360 degree sensory window of the vessel lumen if desired. The embodiment shown in FIG. 5a also illustrates the fact that any number of FBGs 74 and sensor stations 70, 72 may be provided to the guidewire assembly.

Figure 6A:
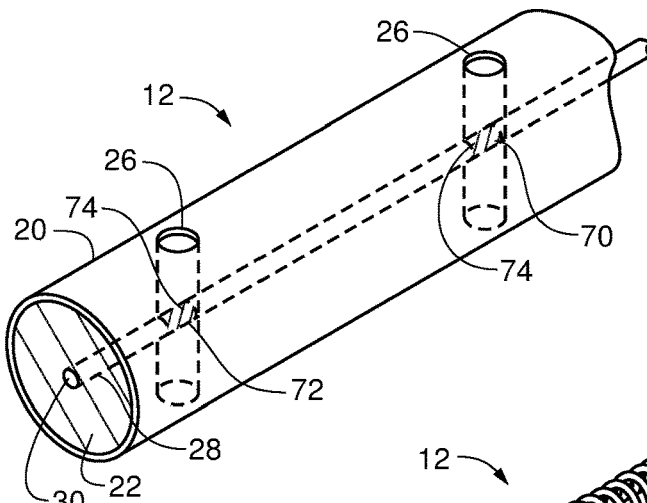
FIG. 6a is a perspective view of an embodiment of a distal end region of the guidewire assembly shown in FIG. 3.
Figure 6B:
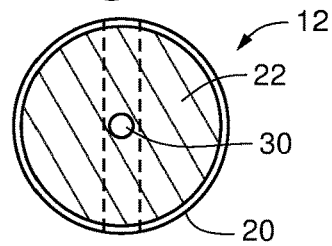

In FIGS. 6a and 6b the guidewire 20 is configured as a hypotube or catheter shaft with lumen 28 extending therethrough. The distal fiber optic wire 30 is contained within the lumen 28. The guidewire shaft 22 will include openings 26 which provide a sensory window corresponding to the position of each sensor station 70 and 72. In the embodiment shown in FIGS. 6a and 6b, an upper and lower opening is provided at each sensor station 70, 72. This exposes both the top and the bottom surface of the sensor stations 70, 72 to the interior of the vessel. In other embodiments, only a single opening to each sensor station 70, 72 is provided through the hypotube. In still further embodiments, three or more openings are provided to expose each sensor station 70, 72 to three or more locations in the vessel. In these embodiments, it is anticipated that each opening 26 will extend radially outward from the distal fiber optic wire 30, with the fiber optic wire 30 residing approximately at the center of the hypotube. However, other orientations of the openings 26 and the fiber optic wire 30 within the hypotube are within the scope of the present disclosure.

Figure 7A:
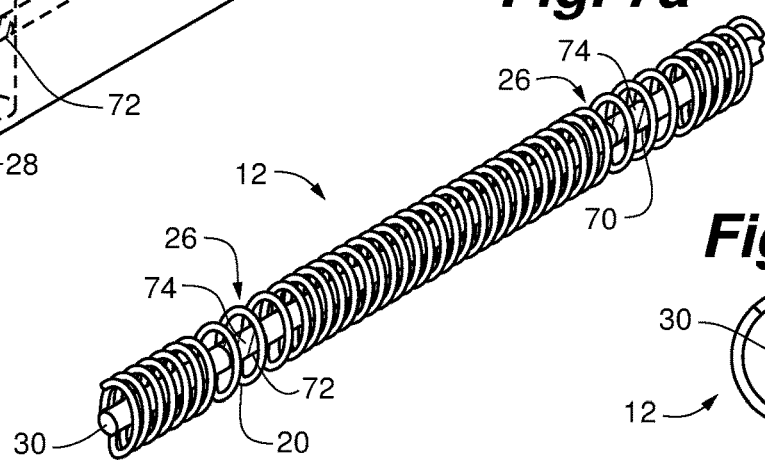
FIG. 7a is a perspective view of an embodiment of a distal end region of the guidewire assembly shown in FIG. 3.
Figure 7B:
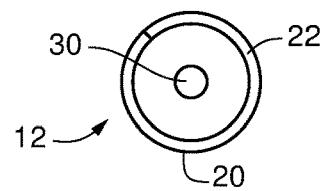

In FIGS. 7a and 7b, an example of the guidewire assembly 12 is shown wherein the guidewire 20 is a singular filar coil or multifilar coils which define a lumen 28 through which the distal fiber optic wire 30 extends. The pitch of the space wound coils 29 are configured such that the coils 29 form openings 26 which allow the sensor stations 70 and 72 unimpeded exposure to the vessel environment (see FIG. 2). Importantly, the configuration of FIGS. 7a and 7b allow the sensor stations 70 and 72 to be exposed in all directions to the interior of the vessel, which allows a single sensor station 70 or 72 to provide a 360 degree sensory window of the vessel lumen.

In the various embodiments shown and described above the distal fiber optic wire 30 contains at least two sensor stations 70 and 72. As is shown in FIG. 2, in order to conduct simultaneous FFR the distal station 70 is positioned distal or upstream of the affected region 102 and the proximal station 72 is positioned proximal or downstream of the affected region 102. Light transmitted through the distal optical fiber 30 interacts with the FBGs 74 of each sensor station to provide a measurable pressure reading on each side of the affected region 102 simultaneously.

Note: the phrase "simultaneous FFR" and the word "simultaneously" are used in this context to differentiate the system 10 of the present disclosure from conventional FFR systems and techniques. Known systems measure pressure (or other vessel characteristics) on each side of the affected regions at distinctly different times as necessitated by the need to reposition the guidewire and sensor mounted thereon. Embodiments of the present invention using two sensor stations 70 and 72, positioned in the manner shown in FIG. 2, provide two sensed pressure values at essentially the speed of the light through the fiber optic wire 30. While there is a distance separating the two sensors 70 and 72, since the pressure sensors are in effect functioning at the speed of light, the difference in time between measurements is for all practical purposes indistinguishable, and are thus: simultaneous.

Figure 8:
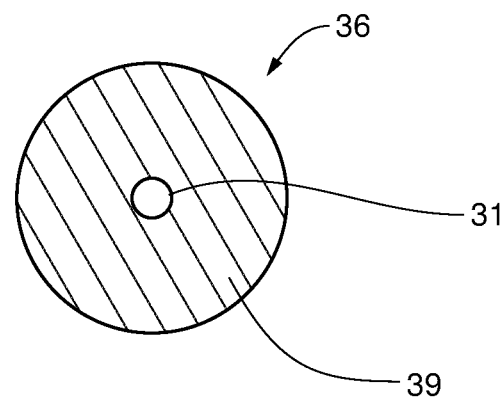
FIG. 8 is a cross-sectional view of a portion of the proximal fiber optic wire shown in FIG. 3 comprised of a single mode fiber.
Figure 9:
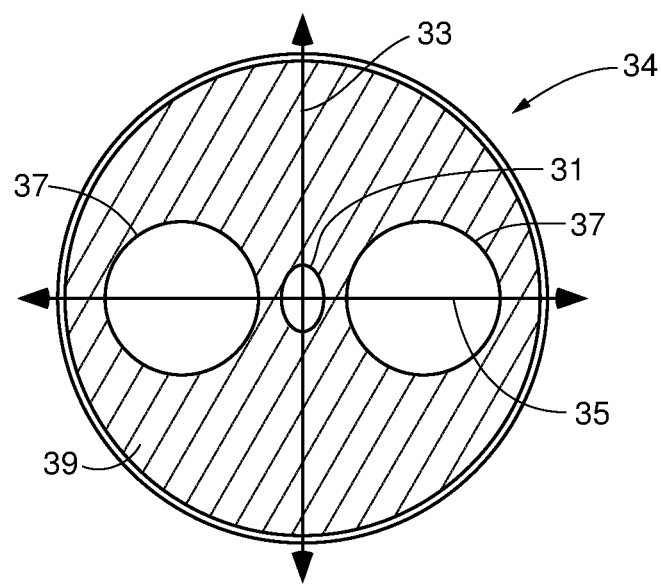
FIG. 9 is a cross-sectional view of a portion of the distal fiber optic wire shown in FIGS. 3-7b comprised of a birefringent fiber.

One embodiment of the present invention uses a polarization maintaining (PM), twin-hole fiber 34, such as is shown in FIG. 9, for the distal optical fiber 30 (and the placement of FBGs 74 therein). This type of PM fiber contains two holes 37 in the cladding 39 that surrounds an elliptical core 31 of the fiber 34. This construction of the polarization-maintaining fiber 34 provides a specific birefringence which maintains the polarization of light in the core 31 along the two main axis illustrated by arrows 33 and 35. Each axis 33 and 35 has a different refractive index, and hence a different light velocities (frequently referred to as the "fast" and "slow" axis), which helps to maintain the polarization of the light along these two axes 33, 35. In this manner, the PM fiber 34 shown in FIG. 9 has a fundamentally different construction than the single mode (or "SM") fiber 36 shown in FIG. 8, in which the core 31 has a circular cross-section and no holes exist in the cladding 39 that surrounds the core 31.

As may be seen in FIGS. 2 and 3a-3b, in order to protect the distal most end of the twin-hole fiber 34 and ensure that blood or other bodily fluid does not enter the holes 37 during use of the system 10, the distal tip of the guidewire assembly 12 includes a length of coreless fiber 41 spliced to the end of the fiber 34. The coreless fiber 41 also acts to minimize back reflections within the optical fiber 34 and to seal the holes in the twin-hole fiber 34.

The size of the holes 37 found in the cladding impact the pressure sensitivity of the twin-hole fiber 34, with larger hole sizes causing the twin-hole fiber 34 to become more sensitive to pressure. In addition, the elliptical configuration of the core 31 further increases the pressure sensitive nature of the fiber 34.

In some embodiments the core 31 has a diameter along the x-axis 33 of approximately 5 μm and a diameter along the y-axis of about 10 μm.

The holes 37 will have a diameter selected to enhance the wire's sensitivity to pressure. The holes may be any of a variety of diameters within the range of about 10 μm to about 25 μm.

In some embodiments the fiber 34 may have a diameter of less than 75 μm. At least one embodiment the polarization maintaining fiber 34 has a diameter of about 75 μm to about 85 μm. In at least one embodiment the diameter is about 80 μm. In some embodiments the fiber may have an external coating of polyamide or similar material having a thickness of approximately 10 μm (which correspondingly increases the total diameter of the fiber 34).

Figure 10A:
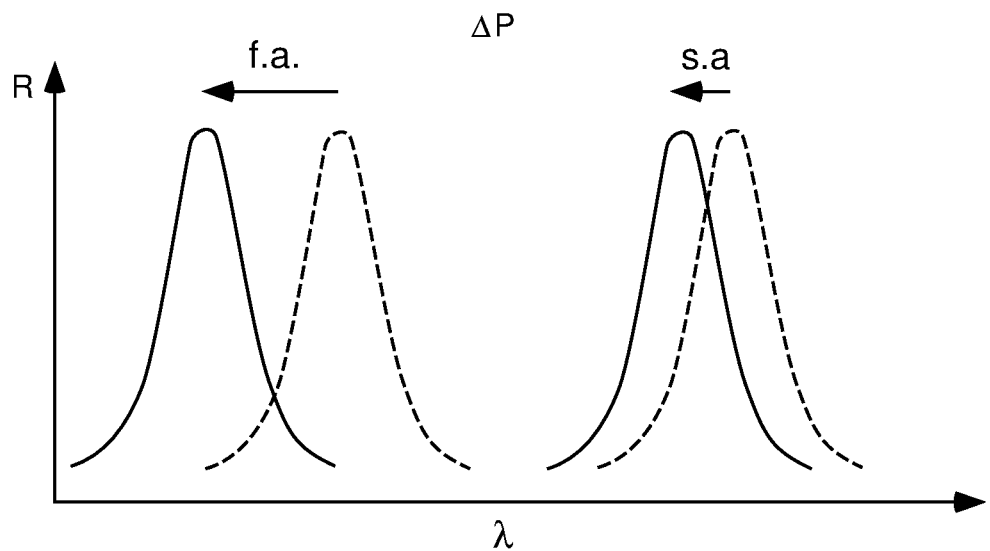
FIG. 10a is a graphical representation of the peak shift of light passed through a birefringent optical fiber affected by pressure.

As mentioned above, sensor stations 70 and 72 each include a unique fiber Bragg grating (FBG). An FBG is a periodic modulation of the refractive index along a fiber optic core. The periodicity results in reflection of light waves that match the periodic spacing of the FBG wavelength while other wavelengths are transmitted unperturbed. The wavelength that is reflected by the FBG is determined by "effective refractive index" of the grating in the fiber core and the period of the grating. In a polarization maintaining fiber optic wire, each polarization mode has a different refractive index and hence results in a different effective refractive index for the FBG. Thus, while a single FBG in a standard, single mode fiber optic wire will reflect light waves of a wavelength centered around a single wavelength, the differing refractive indexes in the two polarization modes in a polarization maintaining fiber optic wire will result in the reflection of light waves centered around two different wavelengths—one for each polarization mode. FIG. 10a shows a graph of the intensity of reflected light according to wavelength. Looking first at the dotted lines, two intensity peaks are shown at two different wavelengths. These peaks show the different reflective characteristics of a single FBG for the fast and slow axis of a polarization maintaining fiber. As shown in this figure, the fast axis polarization mode reflects at a lower wavelength than the slow axis polarization mode. In some embodiments, a u-phase-shifted FBG is used in the fiber, as u-phase-shifted FBGs have been experimentally shown to narrow the spread of wavelengths of reflected light from an FBG on a twin-hole, birefringent fiber. A u-phase-shifted FBG can conceptually be considered as two immediately adjacent FBGs that form an Fabry-Perot resonator.

Figure 10B:
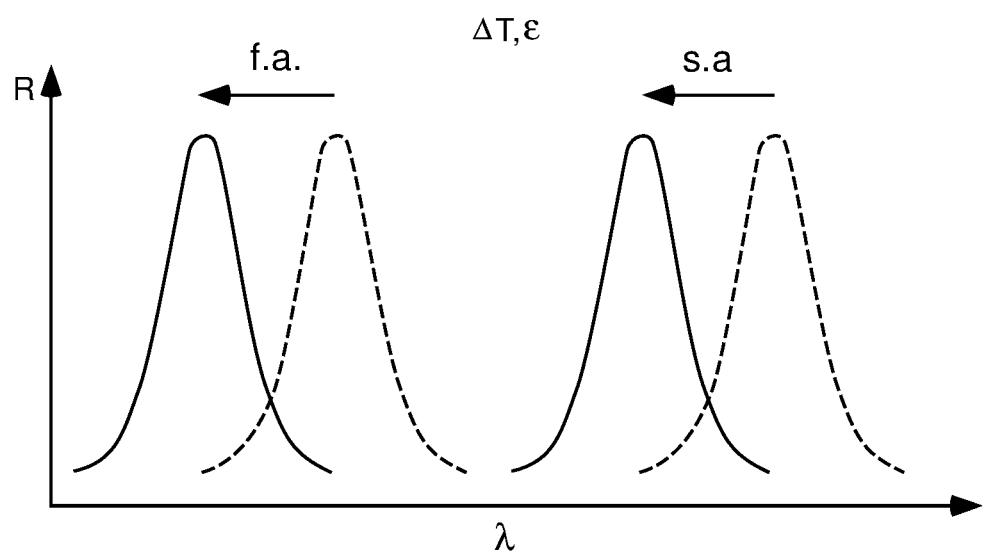
FIG. 10b is a graphical representation of the peak shift of light passed through a birefringent optical fiber affected by temperature and strain.

Various environmental conditions, such as temperature, pressure, and strain can affect the refractive index and grating period of the FBG 74 due to photoelastic and thermooptical effects, and result in a small wavelength shift of the reflective peaks. This shift can be detected, analyzed and displayed as a value allowing the FBG 74 to be used as a sensor. FIG. 10b shows the wavelength shifts that result from either a change in temperature at the FBG or the addition of strain on the fiber optic wire. The dotted peaks show the original peaks for the fast and slow axis signals, respectively. The solid line shows the change in wavelength characteristics of the light reflected from the FBG due to a temperature change, added strain, or both. As shown in FIG. 10b, the change to both the fast axis 33 signal and the slow axis 35 signal are identical for temperature and strain (see FIG. 9 for illustration of axes 33 and 35). In other words, the difference in wavelengths between the peaks of the fast and slow axis signal is unchanged with temperature change (T) and strain (E) on the FBG sensor. Returning to FIG. 10a, the solid lines show the change in wavelength characteristics of the light reflected from the FBG due to a change in pressure on the fiber optic wire at the FBG. As shown, the fast axis signal is changed significantly more than the slow axis signal as a result of the pressure change (P). This is especially so when the polarity-maintaining fiber is a twin hole fiber (as opposed to a Panda or bowtie) fiber, such as is illustrated in FIG. 9, which is perhaps due to the axial compressibility of the twin hole fiber. Thus, a system that can detect changes in the wavelength difference between the reflected fast axis and slow axis signals will be able to detect and measure pressure changes at the FBG sensor, and this system will not be influenced by temperature variations and strain at the sensor.

Figure 12:
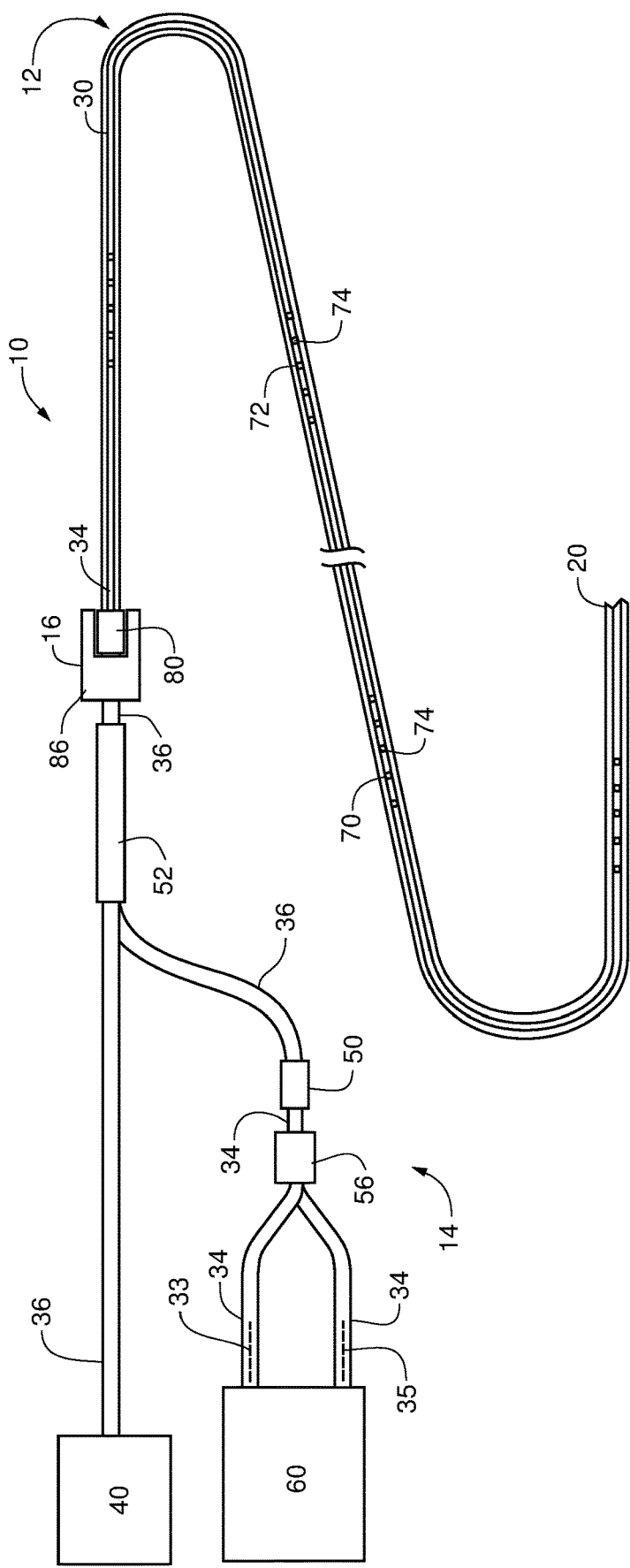
FIG. 12 is a schematic view of an embodiment of the guidewire system.
Figure 13:
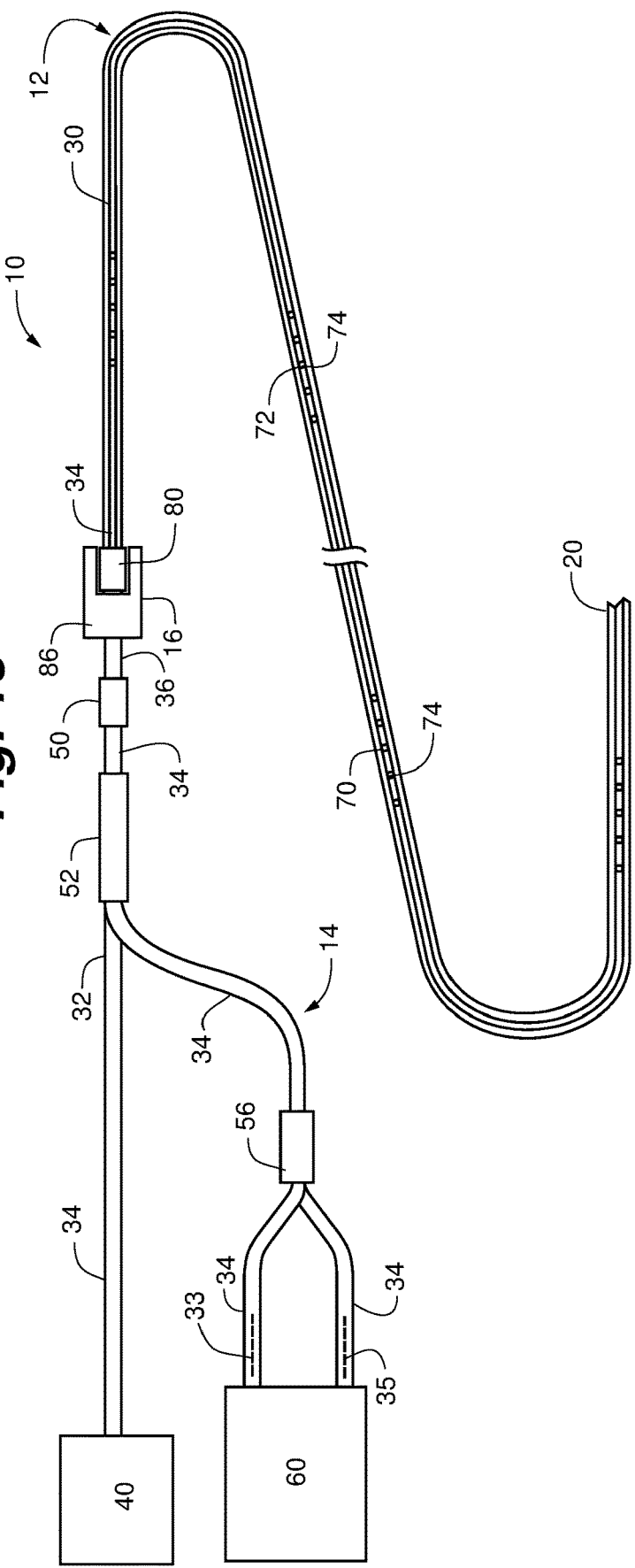
FIG. 13 is a schematic view of an embodiment of the guidewire system.

As shown in the embodiments depicted in FIGS. 3, 12, and 13, an interrogator or reflected light receiver 60 eventually receives the reflected light from each FBG 74. As indicated, the FBG 74 is configured to transduce a pressure change into a reflected wavelength change (such as is depicted in FIG. 10a). The reflected light receiver 60 detects the wavelength change and displays the wavelength change as a pressure. In one embodiment, the reflected light receiver 60 includes light sensors that are sensitive to particular wavelengths of light as well as a processor that detects the wavelengths of the received light, analyzes the detected wavelengths, and applies a conversion formula or table to convert the detected wavelength shifts into a pressure value. The processor and the sensor may be manufactured together into a single chip or component, or may be manufactured as separate chips and/or components that interact via known techniques for data communications.

If multiple FBGs 74 are placed in one fiber 30, with different grating periods, each FBG will provide different peak reflection wavelengths. It may be preferable to select FBGs wavelength characteristics such that the reflected signals do not overlap in wavelength output. In the context of a polarization maintaining fiber optic wire, each FBG will result in a pair of peak reflection wavelengths, with each pair separated from each other based on the differing grating periods of the FBGs. In a simultaneous FFR procedure, the pressure values provided from each sensing station 70 and 72 are compared, and the resulting pressure difference is interpreted by programming of the system 10 and/or the physician 100 (see FIG. 2) to determine if the difference in pressure is indicative of a blockage (or other issue) requiring further therapeutic treatment.

Thus, transmission, reflection and analysis of light (peak shift) passed to and received from the FBG 74 (via the optic fibers 30 and 32) of each of the pressure sensing stations 70 and 72 provides simultaneous pressure readings from each station. The physician 100 (or the system 10) may calculate the pressure difference across the affected region 102 and subsequently determine if the difference is indicative of unacceptable flow restriction; and if so, make a therapeutic decision to further treat the affected region such as by balloon angioplasty (POBA), stenting, drug delivery, or any combination thereof.

As discussed above, one aspect of the present disclosure is the use of two sensors 70 and 72 to conduct a simultaneous FFR diagnostic procedure. It should also be noted, that many benefits of the system 10 apply equally to an embodiment having only a single sensor 70. Providing a guidewire assembly 12 with a single sensor 70 which can accurately detect a pressure value without interference from other vessel characteristics such as temperature and strain; and without the need of additional structures such as surrounding membranes is also an inventive aspect of the present system 10.

Returning to the system 10 as depicted in FIGS. 1-3, the guidewire assembly 12 is manipulated and repositioned as the distal end region of the assembly 12 is advanced through the vasculature to the site of a vessel lesion or other affected area 102. As the guidewire 20 is manipulated, the distal fiber optic wire 30 can be twisted and repositioned making it difficult or impossible to maintain its rotational orientation relative to the detection and analysis apparatus (discussed in detail below) of the proximal assembly 14. To ensure proper transmission of light through the fiber optic line, the line includes a connector 16 which connects the polarization maintaining fiber 34 (note: the distal fiber optic wire 30 is composed of the aforementioned polarization maintaining fiber 34 for its entire length) to a single mode optical fiber 36, such as is shown in FIG. 8, and which comprises at least a portion of the proximal fiber optic wire 32 shown in the system embodiments of FIGS. 3 and 12-13. If the connector 16 attempted to connect the polarization maintaining fiber 34 directly to another polarization maintaining fiber, it would be mandatory that the fast and slow axis of each fiber be perfectly aligned to prevent signal degradation and loss. Maintaining consistent orientation through a connector 16 is extremely difficult, especially when the physical size of the connector 16 must be restricted due to the need to pass a therapeutic catheter over the connector 16 and the guidewire assembly 12. Connecting a single mode fiber 36 to the polarization maintaining fiber 34 through the connector 16 allows the orientation of reflected light signals from the FBG 74 of the sensor stations 70 and 72 to be maintained therethrough regardless of the orientation of the polarization maintaining fiber 34 with respect to the single mode fiber 36.

Connector 16 provides a necessary interface between the polarization maintaining fiber 34 of the distal fiber optic wire 30 and the single mode fiber 36, but also provides a mechanism for removeably engaging the entire guidewire assembly 12 to and from the proximal assembly 14 so as to allow for greater ease of use during the advancement of the guidewire assembly 12 into position within the vasculature and to allow for use of the guidewire assembly 12 as a conventional guidewire.

An embodiment of connector 16 is depicted in FIG. 11a-11d. As best shown in FIG. 11c the connector 16 is constructed of a male housing 80 and a female housing 86. Within male housing 80 a proximal end 82 of the polarization maintaining fiber 34 is positioned. The male housing 80 may be configured as a proximal most end of the guidewire 20. As shown in FIGS. 11a and 11b, immediately and proximally adjacent to the proximal end 82 of the polarization maintaining fiber 34 is a short length or "splice" 84 of single mode fiber 36, and also contained within the male housing 80. This permanent splice 84 allows two single mode fiber optic wires 36 to be connected together within the connector 16 (although the splice 84 itself could be considered a portion of the connector assembly 16). In other embodiments, no splice 84 is added to the polarization maintaining fiber 34, which allows the connector 16 to directly connect the distal (polarization maintaining) fiber optic wire 30 to the proximal (single mode) fiber optic wire 32.

The male housing 80 is insertable and rotatable within a receiving lumen 88 of the female housing 86, such as is depicted in FIG. 11c. Proximally adjacent to the receiving lumen 88 is positioned the distal end 90 of the single mode fiber 36 of the proximal fiber optic wire 32.

The connector 16 is constructed to allow the guidewire assembly 12 to be removeably engaged to the female housing 86 of the connector 16 and thereby allow the continuous transmission of light between the single mode fiber 36 and the polarization maintaining fiber 34 when the guidewire assembly 12 is engaged thereto. As mentioned above, when the guidewire assembly 12 is connected through the connector 16, the connector also allows the polarization maintaining fiber 34 to freely rotate relative to the single mode fiber portion 36 of the proximal fiber optic wire 32 without interrupting the transmission of light or affecting its polarization. Thus, if desired the guidewire assembly 12 may be manipulated while connected to the rest of system 10 without risk of signal loss or damage to the fiber optic line regardless of its orientation or position.

The guidewire assembly 12 may be disconnected from the connector 16 at any time during or after the FFR diagnostic procedure. In at least one embodiment, the guidewire assembly 12 is disconnected from the connector 16 after the diagnosis of the affected region 102 (see FIG. 2) is complete in order to allow the guidewire assembly 12 to act as a conventional guidewire for a subsequent angioplasty, stent delivery or other therapeutic procedure if called for.

In at least one embodiment, such as is shown in FIG. 11d the connector 16 connects only the optic fibers 34 and 36, while the guidewire 20 remains disconnected or otherwise free to be manipulated by the physician 100 (see FIG. 2). In the embodiment shown in FIG. 11d the connector 16 comprises a single housing 81 which contains a micro-sleeve 83 into which the proximal end 82 of the polarization maintaining fiber 34 is inserted as well as the distal end 90 of the single mode fiber portion 36.

As shown in FIG. 3, the single mode fiber 36 exits proximally from the connector 16 and extends to the proximal assembly 14. The proximal assembly 14 may be an assembly of individual components or may be combined into a single device. The proximal assembly comprises the proximal fiber optic wire 32, a light source 40, a polarization control unit 50, and a light detection element or receiver 60.

Some specific arrangements and example embodiments of the proximal assembly 14 are shown in FIGS. 12 and 13. As will be understood by one of ordinary skill, the embodiments shown in FIGS. 12 and 13 include components such as polarization control unit 50, a circulator 52, etc. While these devices are known and their function in controlling and analyzing light signals are well understood, optimization of their use and their position within specific embodiments of the system 10 are aspects of the disclosure. For example, the particular arrangement of the polarization control unit 50 and circulator 52, as well as the particular use and placement of single mode fiber 36 and polarization maintaining fiber 34 depend on the particular type and characteristics of the light source 40.

In the embodiment shown in FIG. 12, the light source 40 is one or more Superluminescent Light Emitting Diodes (SLED). SLEDs provide a broad spectrum, of a polarized or unpolarized light signal. IF the SLED is unpolarized then light is transmitted at every polarization angle. In the unpolarized SLED case, such as is shown in FIG. 12 a single mode fiber 36 is used to carry the light through the circulator 52 and into the connector 16. When the light passes from the single mode fiber 36 to the polarization maintaining fiber 34 of the guidewire assembly 12, only the power aligning along the slow and fast axis (see FIG. 9) will be transmitted. After the light is reflected from the FBGs 74 of the sensors 70 and 72 and passes back through the connector 16 light re-enters the single mode fiber 36 and is transmitted into the circulator 52.

Known circulators generally have the same fiber modes at both their entrance port and exit port. The unpolarized light of the SLED initially uses the single mode fiber 36, thus this type of optic fiber is maintained at all ports of the circulator 52 in FIG. 12. Thus, single mode fiber 36 carries the reflected light from the circulator to the polarization controller 50. The reflected light enters the polarization controller 50 via single mode fiber 36.

Polarization controllers manipulate the state of polarization within a single mode fiber, and can be used to align polarization in a single mode fiber for transmission into a polarization-maintaining fiber. Polarization controllers are well known in the prior art and are available from a number of manufacturers, including OZ Optics, Ltd. of Abu Dhabi, United Arab Emirates. The polarization controller 50 shown in FIG. 12 ensures the correct alignment of the reflected light signal before the light travels into polarization maintaining fiber optic wire 34 and to a polarizing beam splitter 56. In effect, the polarization controller 50 allows the limited use of single mode fiber 36 to receive polarized signals from the polarization maintaining fiber 34 at connector 16 (thereby avoiding the difficulties of aligning two polarization maintaining fibers 34 at the connector 16). Since the polarization of light can deteriorate when traveling through single mode fiber 36, the polarization controller 50 allows the polarized signals in the single mode fiber 36 to be inserted back into polarization maintaining fiber 34 and avoid excessive deterioration.

At the polarization beam splitter 56, the fast axis 33 peak shift and slow axis 35 peak shift (light corresponding to axis 33 and 35 are represented by the labeled dotted lines—see also the discussion above and FIGS. 9 and 10 for additional illustration) are divided onto separate fibers and presented for analysis to an optic sensing microchip, interrogator or other analysis mechanism collectively referred to herein as the reflected light receiver 60.

In the embodiment shown in FIG. 13, a different light source 40 is used. Here the light source 40 is a polarized light source such as: one or more lasers or one or more polarized SLEDs. In embodiments where the light source 40 comprises one or more laser, the lasers may be selected from a scanning or non-scanning type laser.

In the embodiment shown in FIG. 13, light from the polarized light source 40 is transmitted directly into polarization-maintaining optical fibers 34 and transmitted through a circulator 52 still on polarization-maintaining fiber 34. Because polarized light from the lasers is entering the polarization-maintaining fiber 34, the preferred embodiment ensures that the single polarization of light from the lasers enters at an angle approximately intermediate to the fast axes 33 and the slow axis 35 of the polarization-maintaining fiber 34 so that the light passes approximately equally into both polarization modes of the fiber 34. The light then passes through the polarization controller 50 and emerges on a short single mode fiber 36 before entering the connector 16 and into the distal fiber optic wire 30. The signal reflected back from the FBG 74 then passes back through the proximal connector 16 into the single mode fiber 36. The polarization controller 50 then manipulates the polarization of the signals in the single mode fiber 36 so as to properly pass the signals back to the polarization maintaining fiber 34. At that point, the signals in the polarization maintaining fiber 34 pass back through the circulator 52 to the polarizing beam splitter 56 and reflected light receiver 60.

The reflected light receiver 60 converts the detected light signals corresponding to axes 33 and 35 into pressure values using a scale that is experimentally determined for a given fiber/FBG combination. The FBG reflection spectra corresponding to the detected light form a linear relationship to the determined pressure values. In some embodiments the reflected light receiver 60 is configured to further calculate an if the pressure values meet or exceed a threshold (outside the established linear relationship) that is indicative of the need for additional therapeutic treatment as discussed in greater detail above.

Mathematically speaking, the relationship between the change in pressure (P) and the change in temperature (T)

provided by the difference in wavelength (between the fast axis (x) 33 and the slow axis (y) 35 can be represented by the following matrix:

$$\begin{pmatrix} \Delta T \\ \Delta P \end{pmatrix} = \begin{bmatrix} \delta\lambda_x/\delta T & \delta\lambda_x/\delta P \\ \delta\lambda_y/\delta T & \delta\lambda_y/\delta P \end{bmatrix}^{-1} \begin{pmatrix} \Delta\lambda_x \\ \Delta\lambda_y \end{pmatrix}$$

It should be recognized that the embodiments shown in FIGS. 12 and 13 are merely two examples of how the components of the proximal assembly 14 may be arranged. Other alternatives exist and are aspects of the present disclosure. For example, a polarizer could be used to polarize light emitted from an SLED light source 40 to match the input port of the polarizing beam splitter 56 and reflected light receiver 60, etc.

As mentioned above, the present system 10 does not require the use of a membrane at or around the FBGs 74 to amplify or enhance the affects of pressure on the sensor stations 70 and 72. However, in at least one embodiment a membrane or other structure may be included in the sensor stations 70 and 72 of the polarization maintaining fiber 34 to enhance the affects of pressure on the FBG 74.

The many features and advantages of the invention are apparent from the above description. Examples of embodiments of the present disclosure are also represented in the following numbered paragraphs:

Paragraph 1. A pressure sensing system comprises a light source, a reflected light receiver, a distal polarization maintaining fiber optic wire in communication with the light source and the reflected light receiver, and a guidewire having a guidewire body that supports the distal polarization maintaining fiber optic wire. The distal fiber optic wire has at least one pressure sensing station. The at least one pressure sensing station comprises a fiber Bragg grating (FBG) in the distal polarization maintaining fiber optic wire. The at least one pressure sensing station being in direct exposure to environment pressures adjacent thereto. The FBG configured to transduce a detected pressure into a reflected wavelength change. The reflected light receiver configured to detect the reflected wavelength change and determine a pressure value.

Paragraph 2. The system of paragraph 1, wherein the distal polarization maintaining fiber optic wire has two polarization modes with different refractive indexes that reflect different light wavelengths at the FBG. The FBG is configured to transduce the detected pressure by having the detected pressure vary the reflected wavelengths at the FBG differently between the two polarization modes.

Paragraph 3. The system of paragraph 2, wherein the distal polarization maintaining fiber optic wire is a twin-hole fiber with an elliptical core.

Paragraph 4. The system of paragraph 1, wherein the system further comprises a proximal pressure sensing station and a distal pressure sensing station. The proximal pressure sensing station and the distal pressure sensing station each configured to detect a pressure measurement simultaneously.

Paragraph 5. The system of paragraph 1, wherein the system has a proximal assembly, a guidewire assembly and a connector therebetween. The proximal assembly comprises the light source and the reflected light receiver. The guidewire assembly comprises the guidewire and the distal fiber optic wire.

Paragraph 6. The system of paragraph 5, wherein the proximal assembly further comprises a single mode fiber optic wire. The connector configured to releasably and rotatably connect the polarization maintaining fiber optic wire of the guidewire assembly to the single mode fiber optic wire of the proximal assembly.

Paragraph 7. The system of paragraph 6, wherein the connector comprises a female housing, a male housing and a length of single mode fiber optic wire. The length of single mode fiber optic wire is contained in the male housing. A proximal most end of the polarization maintaining fiber optic wire of the guidewire assembly is contained in the male housing adjacent to the length of single mode fiber optic wire. The male housing is constructed and arranged to be removeably engaged to the female housing. The male housing being rotatable relative to the female housing when engaged thereto.

Paragraph 8. The system of paragraph 7, wherein the female housing contains a distal most end of the single mode fiber optic wire of the proximal assembly. When the male housing is engaged to the female housing the length of single mode fiber optic wire contained in the male housing is in communication with the single mode fiber optic wire of the proximal assembly and the polarization maintaining fiber optic wire of the guidewire assembly.

Paragraph 9. The system of paragraph 8, wherein the male housing is a proximal end of the guidewire.

Paragraph 10. The system of paragraph 7, wherein the proximal assembly further comprises a circulator. The single mode fiber optic wire within the female housing extends proximally from the connector to communicate with the circulator.

Paragraph 11. The system of paragraph 10, wherein the light source is a superluminescent light emitting diode. The superluminescent light emitting diode is in communication with the circulator via single mode fiber optic wire.

Paragraph 12. The system of paragraph 6, further comprising a polarization controller configured to pass polarized light received on the single mode fiber optic wire from the connector into a proximal polarization maintaining fiber optic wire.

Paragraph 13. The system of paragraph 12, wherein the proximal assembly further comprises a polarizing beam splitter. The polarizing beam splitter in communication with the reflected light receiver and the polarization controller via a polarization-maintaining fiber optic wire.

Paragraph 14. The system of paragraph 7, wherein the proximal assembly further comprises a polarization controller. The single mode fiber optic wire within the female housing extends proximally from the connector to communicate with the polarization controller.

Paragraph 15. The system of paragraph 14, wherein the proximal assembly further comprises a circulator. The circulator in optical communication with the polarization controller via polarization maintaining fiber optic wire.

Paragraph 16. The system of paragraph 15, wherein the proximal assembly further comprises a polarizing beam splitter. The polarizing beam splitter is in communication with the reflected light receiver and the circulator via a polarization-maintaining fiber optic wire.

Paragraph 17. The system of paragraph 1, wherein the guidewire defines a channel. The distal fiber optic wire is at least partially contained within the channel.

Paragraph 18. A pressure sensing guidewire comprises a guidewire body and a polarization maintaining twin-hole fiber optic wire supported by the guidewire body. The polarization maintaining twin-hole fiber has an elliptical core, a first and second fiber Bragg grating (FBG) in the elliptical core. Each FBG is configured to reflect light of differing wavelengths and has a first polarization mode and a second polarization mode. The first polarization mode has a first refractive index and the second polarization mode has a second refractive index, wherein the first and second polarization modes reflect light of differing wavelengths at each of the first and second FBGs. A connector connects the polarization maintaining twin-hole fiber optic wire to a single mode fiber.

Paragraph 19. A system for detecting pressure within a body lumen comprises a proximal assembly, a distal assembly and a connector therebetween.

The proximal assembly comprises a light source, a reflected light receiver, and a combination of single mode fiber optic wire and polarization-maintaining fiber optic wire. The distal assembly comprises a guidewire and a distal fiber optic wire. The distal fiber optic wire is comprised of a polarization-maintaining fiber optic wire. The distal fiber optic wire has at least two pressure sensing stations. Each pressure sensing station comprising a fiber Bragg grating (FBG). Each pressure sensing station is directly exposed to environment pressures of the body lumen adjacent thereto. The light source is configured to transmit light through the single mode fiber optic wire and polarization-maintaining fiber to the FBG of each pressure sensing station. The FBG is configured to reflect light back through the polarization-maintaining fiber and single mode fiber optic wire to the reflected light receiver for analysis. The connector is constructed and arranged to maintain the polarization of light passing between the single mode fiber optic wire and the polarization-maintaining fiber optic wire.

Paragraph 20. A method for conducting a simultaneous fractional flow reserve diagnostic procedure comprises the following steps:

providing a system having a guidewire assembly, the guidewire assembly comprising a guidewire and a fiber optic wire in communication with a light source and the reflected light receiver, the fiber optic wire having at least two pressure sensing stations, each pressure sensing stations comprising a fiber Bragg grating (FBG);

advancing the guidewire assembly to an affected region of a vessel such that one of the pressure sensing stations is positioned proximal of the affected region and one of the pressure sensing stations is positioned distal of the affected region;

transmitting light to each from the light source to the FBG of each pressure sensing station via the fiber optic wire;

reflecting light from each FBG to the reflected light receiver via the fiber optic wire;

analyzing reflected light received by the reflected light receiver to determine a pressure measurement at each pressure sensing station;

calculating a pressure difference across the affected region of the vessel by comparing the pressure measurements provided by each pressure sensing station; and determining if the pressure difference across the affected region is sufficient to require additional therapeutic steps.

Numerous modifications and variations of the above will readily occur to those skilled in the art. Since such modifications are possible, the invention is not to be limited to the exact construction and operation illustrated and described. Rather, the present invention should be limited only by the following claims.

What is claimed is:

1. A pressure sensing system configured to detect a pressure in the vasculature of a patient, the pressure sensing system comprising:
 a) a proximal assembly, comprising:
  i) a light source;
  ii) a circulator optically connected to the light source by a fiber optic wire;
  iii) a polarization controller, wherein a single-mode fiber optic wire optically connects the polarization controller to the circulator;
  iv) a polarization beam splitter, wherein a first proximal polarization-maintaining fiber optic wire optically connects the polarization beam splitter to the polarization controller; and
  v) a reflected light receiver optically connected to the polarization beam splitter opposite the polarization controller by a second proximal polarization-maintaining fiber optic wire and a third proximal polarization-maintaining fiber optic wire; and
 b) a distal assembly, comprising:
  i) a guidewire; and
  ii) a distal polarization-maintaining fiber optic wire supported by the guidewire, wherein the distal polarization-maintaining fiber optic wire has at least one fiber Bragg grating (FBG) pressure sensing station that is exposable to environment pressure adjacent thereto; and
 c) an optical connector positioned between the proximal assembly and the distal assembly, the optical connector comprising:
  i) a proximal housing containing a proximal single-mode fiber optic wire, the proximal single-mode fiber optic wire extending from a proximal single-mode fiber optic wire proximal end to a proximal single-mode fiber optic wire distal end, wherein the proximal end of the proximal single-mode fiber optic wire is optically connected to the circulator opposite the light source and the polarization controller; and
  ii) a distal housing that is removably mateable with the proximal housing and contains a distal single-mode fiber optic wire, the distal single-mode fiber optic wire extending from a distal single-mode fiber optic wire proximal end to a distal single-mode fiber optic wire distal end,
  iii) wherein a proximal end of the distal polarization-maintaining fiber optic wire supported by the guidewire is contained in the distal housing optically connected to the distal end of the distal single-mode fiber optic wire, and
  iv) wherein, when the distal housing is mated with the proximal housing, the proximal end of the distal single-mode fiber optic wire contained in the distal housing is optically connected to the distal end of the proximal single-mode fiber optic wire contained in the proximal housing, and
 d) wherein, when the guidewire is introduced into the vasculature of a patient, the light source is configured to transmit light along the fiber optic wire to the circulator and in turn to the proximal single-mode fiber optic wire, the distal single-mode fiber optic wire, and the distal polarization-maintaining fiber optic wire to the at least one fiber Bragg grating (FBG) pressure sensing station, and
 e) wherein the at least one FBG pressure sensing station is configured to transduce a detected pressure into a reflected wavelength change that is optically transmittable as a polarized light along the distal polarization-maintaining fiber optic wire, the distal single-mode fiber optic wire, the proximal single-mode fiber optic wire optically connected to the circulator and in turn to the polarization controller optically connected to the polarization beam splitter by the first proximal polarization-maintaining fiber optic wire, the polarization beam splitter serving to split the reflected polarized light into its two polarizations that are optically transmitted to the reflected light receiver by the respective second and third polarization-maintaining fiber optic wires, the reflected light receiver being configured to detect the reflected wavelength changes for each polarization of the at least one FBG pressure sensing station to thereby determine a pressure value in the vasculature of the patient.

2. The pressure sensing system of claim 1, wherein the distal polarization-maintaining fiber optic wire is a twin-hole fiber with an elliptical core.

3. The pressure sensing system of claim 1, wherein the distal polarization-maintaining fiber optic wire comprises a proximal FBG as a proximal pressure sensing station and a distal FBG as a distal pressure sensing station, and wherein the proximal and distal FBG pressure sensing stations are each configured to detect a pressure measurement simultaneously.

4. The pressure sensing system of claim 1, wherein the distal housing is rotatable relative to the proximal housing when mated thereto so that the distal and proximal single-mode fiber optic wires are rotatable with respect to each other.

5. The pressure sensing system of claim 1, wherein the distal housing is a proximal end of the guidewire.

6. The pressure sensing system of claim 1, wherein the light source is a superluminescent light-emitting diode that is optically connected to the circulator via the fiber optic wire.

7. The pressure sensing system of claim 1, wherein the guidewire defines a channel, and wherein the distal polarization-maintaining fiber optic wire is at least partially contained within the channel.

8. A system for detecting pressure within a body lumen, the system comprising:
    a) a proximal assembly, comprising:
        i) a light source;
        ii) a circulator optically connected to the light source by a fiber optic wire;
        iii) a polarization controller, wherein a single-mode fiber optic wire optically connects the polarization controller to the circulator;
        iv) a polarization beam splitter, wherein a first proximal polarization-maintaining fiber optic wire optically connects the polarization beam splitter to the polarization controller; and
        v) a reflected light receiver optically connected to the polarization beam splitter opposite the polarization controller by a second proximal polarization-maintaining fiber optic wire and a third proximal polarization-maintaining fiber optic wire; and
    b) a distal assembly, comprising:
        i) a guidewire; and
        ii) a distal polarization-maintaining fiber optic wire supported by the guidewire, the distal polarization-maintaining fiber optic wire having at least two fiber Bragg grating (FBG) pressure sensing stations that are both exposable to environmental pressure adjacent thereto; and
    c) an optical connector positioned between the proximal assembly and the distal assembly, the optical connector comprising:
        i) a proximal female housing containing a proximal single-mode fiber optic wire, the proximal single-mode fiber optic wire extending from a proximal single-mode fiber optic wire proximal end to a proximal single-mode fiber optic wire distal end, wherein the proximal end of the proximal single-mode fiber optic wire is optically connected to the circulator opposite the light source and the polarization controller; and
        ii) a proximal end of the guidewire being removably mateable with the proximal housing and containing a distal single-mode fiber optic wire, the distal single-mode fiber optic wire extending from a distal single-mode fiber optic wire proximal end to a distal single-mode fiber optic wire distal end,
        iii) wherein a proximal end of the distal polarization-maintaining fiber optic wire supported by the guidewire is contained in the guidewire optically connected to the distal end of the distal single-mode fiber optic wire, and
        iv) wherein, when the proximal end of the guidewire is mated with the proximal female housing, the proximal end of the distal single-mode fiber optic wire contained in the guidewire is optically connected to the distal end of the proximal single-mode fiber optic wire contained in the female housing, and
    d) wherein, when the guidewire is introduced into the vasculature of a patient, the light source is configured to transmit light through the fiber optic wire to the circulator and in turn the proximal single-mode fiber optic wire optically connected to the distal single-mode fiber optic wire and the distal polarization-maintaining fiber optic wire having the at least two FBG pressure sensing stations, and
    e) wherein the at least two FBG pressure sensing stations are configured to transduce a detected pressure into a reflected wavelength change that is optically transmittable as a polarized light along the distal polarization-maintaining fiber optic wire, the distal single-mode fiber optic wire, the proximal single-mode fiber optic wire optically connected to the circulator and in turn the polarization controller optically connected to the polarization beam splitter by the first proximal polarization-maintaining fiber optic wire, the polarization beam splitter serving to split the reflected polarized light from each of the at least two FBG pressure sensing stations into its two polarizations that are optically transmitted to the reflected light receiver by the respective second and third polarization-maintaining fiber optic wires, the reflected light receiver being configured to detect the reflected wavelength changes for each polarization to thereby determine a pressure value in the vasculature of the patient.

9. A method for conducting a simultaneous fractional flow reserve diagnostic procedure, comprising the steps of:
    a) providing a system, comprising:
        i) a proximal assembly, comprising:
            A) a light source;
            B) a circulator optically connected to the light source by a fiber optic wire;
            C) a polarization controller, wherein a single-mode fiber optic wire optically connects the polarization controller to the circulator;

D) a polarization beam splitter, wherein a first proximal polarization-maintaining fiber optic wire optically connects the polarization beam splitter to the polarization controller; and
E) a reflected light receiver optically connected to the polarization beam splitter opposite the polarization controller by a second proximal polarization-maintaining fiber optic wire and a third proximal polarization-maintaining fiber optic wire; and
ii) a distal assembly, comprising:
A) a guidewire; and
B) a distal polarization-maintaining fiber optic wire supported by the guidewire, wherein the distal polarization-maintaining fiber optic wire has at least two fiber Bragg grating (FBG) pressure sensing stations that are exposable to environment pressure adjacent thereto; and
iii) an optical connector positioned between the proximal assembly and the distal assembly, wherein the optical connector comprises:
A) a proximal housing containing a proximal single-mode fiber optic wire, the proximal single-mode fiber optic wire extending from a proximal single-mode fiber optic wire proximal end to a proximal single-mode fiber optic wire distal end, wherein the proximal end of the proximal single-mode fiber optic wire is optically connected to the circulator opposite the light source and the polarization controller; and
B) a proximal end of the guidewire being removably mateable with the proximal housing and containing a distal single-mode fiber optic wire, the distal single-mode fiber optic wire extending from a distal single-mode fiber optic wire proximal end to a distal single-mode fiber optic wire distal end,
C) wherein a proximal end of the distal polarization-maintaining fiber optic wire supported by the guidewire is optically connected to the distal end of the distal single-mode fiber optic wire, and
D) wherein, when the proximal end of the guidewire is mated with the proximal housing, the proximal end of the distal single-mode fiber optic wire contained in the guidewire is optically connected to the distal end of the proximal single-mode fiber optic wire contained in the proximal housing; and
b) advancing the guidewire to an affected region of the vasculature so that a proximal one of the at least two FBG pressure sensing stations positioned proximal the affected region is exposed to pressure at a first location in the vasculature and a distal one of the at least two FBG pressure sensing stations positioned distal the affected region is exposed to pressure at a second location in the vasculature;
c) transmitting light from the light source along the fiber optic wire to the circulator and in turn to the proximal single-mode fiber optic wire, the distal single-mode fiber optic wire, and the distal polarization-maintaining fiber optic wire to the at least two FBG pressure sensing stations;
d) reflecting light as a polarized light from the at least two FBG pressure sensing stations to the reflected light receiver via the distal polarization-maintaining fiber optic wire, the distal single-mode fiber optic wire, the proximal single-mode fiber optic wire optically connected to the circulator and in turn the polarization controller optically connected to the polarization beam splitter by the first proximal polarization-maintaining fiber optic wire, the polarization beam splitter serving to split the reflected polarized light into its two polarizations that are optically transmitted to the reflected light receiver by the respective second and third polarization-maintaining fiber optic wires;
e) analyzing the reflected light received by the reflected light receiver to determine a pressure measurement at each of the first and second locations of the respective at least two FBG pressure sensing stations;
f) calculating a pressure difference across the affected region of the vasculature by comparing the pressure measurements provided by the at least two FBG pressure sensing stations; and
g) determining if the pressure difference across the affected region is sufficient to require additional therapeutic steps.

10. The pressure sensing system of claim 1, wherein the proximal housing is a female housing and the distal housing is a male housing that is releasably and rotatably mateable with the proximal female housing or, the proximal housing is a male housing and the distal housing is a female housing that is releasably and rotatably mateable with the proximal male housing.

11. The pressure sensing system of claim 1, wherein at least one sensory window extends radially from an outer surface of the guidewire to the at least one FBG pressure sensing station so that the at least one FBG pressure sensing station is directly exposable to environment pressure through the at least one radially intersecting sensory window.

12. The pressure sensing system of claim 1, wherein two diametrically opposed sensory windows extend radially from an outer surface of the guidewire to the at least one FBG pressure sensing station so that the at least one FBG pressure sensing station is directly exposable to environment pressure through the two radially intersecting sensory windows.

13. The pressure sensing system of claim 1, wherein three sensory windows extend radially from an outer surface of the guidewire to the at least one FBG pressure sensing station so that the at least one FBG pressure sensing station is directly exposable to environment pressure through the three radially intersecting sensory windows.

14. The pressure sensing system of claim 1, wherein the fiber optic wire optically connecting the light source to the circulator is either a single-mode fiber optic wire or a second proximal polarization-maintaining fiber optic wire.

15. The pressure sensing system of claim 1, wherein the light source is a laser.

16. The system of claim 8, wherein the fiber optic wire optically connecting the light source to the circulator is either a single-mode fiber optic wire or a second proximal polarization-maintaining fiber optic wire.

17. The method of claim 9, including providing the fiber optic wire optically connecting the light source to the circulator as either a single-mode fiber optic wire or a second proximal polarization-maintaining fiber optic wire.

18. A pressure sensing system configured to detect a pressure in the vasculature of a patient, the pressure sensing system comprising:
a) a proximal assembly, comprising:
i) a light source;
ii) a circulator optically connected to the light source by a fiber optic wire;
iii) a polarization controller, wherein a single-mode fiber optic wire optically connects the polarization controller to the circulator;

iv) a polarization beam splitter, wherein a first proximal polarization-maintaining fiber optic wire optically connects the polarization beam splitter to the polarization controller; and v) a reflected light receiver optically connected to the polarization beam splitter opposite the polarization controller by a second proximal polarization-maintaining fiber optic wire and a third proximal polarization-maintaining fiber optic wire; and b) a distal assembly, comprising:

i) a guidewire; and ii) a distal polarization-maintaining fiber optic wire supported by the guidewire, wherein the distal polarization-maintaining fiber optic wire has at least one fiber Bragg grating (FBG) pressure sensing station that is exposable to environment pressure adjacent thereto; and c) an optical connector positioned between the proximal assembly and the distal assembly, the optical connector comprising:

i) a proximal housing containing a proximal single-mode fiber optic wire, the proximal single-mode fiber optic wire extending from a proximal single-mode fiber optic wire proximal end to a proximal single-mode fiber optic wire distal end, wherein the proximal end of the proximal single-mode fiber optic wire is optically connected to the circulator opposite the light source and the polarization controller; and ii) a proximal end of the guidewire being removably mateable with the proximal housing and containing a distal single-mode fiber optic wire, the distal single-mode fiber optic wire extending from a distal single-mode fiber optic wire proximal end to a distal single-mode fiber optic wire distal end, iii) wherein a proximal end of the distal polarization-maintaining fiber optic wire supported by the guidewire is optically connected to the distal end of the distal single-mode fiber optic wire, and iv) wherein, when the proximal end of the guidewire is mated with the proximal housing, the proximal end of the distal single-mode fiber optic wire is optically connected to the distal end of the proximal single-mode fiber optic wire contained in the proximal housing, and d) wherein, when the guidewire is introduced into the vasculature of a patient, the light source is configured to transmit light along the fiber optic wire to the circulator and in turn to the proximal single-mode fiber optic wire, the distal single-mode fiber optic wire, and the distal polarization-maintaining fiber optic wire to the at least one fiber Bragg grating (FBG) pressure sensing station, and e) wherein the at least one FBG pressure sensing station is configured to transduce a detected pressure into a reflected wavelength change that is optically transmittable as a polarized light along the distal polarization-maintaining fiber optic wire, the distal single-mode fiber optic wire, the proximal single-mode fiber optic wire optically connected to the circulator and in turn to the polarization controller optically connected to the polarization beam splitter by the first proximal polarization-maintaining fiber optic wire, the polarization beam splitter serving to split the reflected polarized light into its two polarizations that are optically transmitted to the reflected light receiver by the respective second and third polarization-maintaining fiber optic wires, the reflected light receiver being configured to detect the reflected wavelength changes for each polarization to thereby determine a pressure value in the vasculature of the patient.

19. A pressure sensing system configured to detect a pressure in the vasculature of a patient, the pressure sensing system comprising:

a) a proximal assembly, comprising:

i) a light source;

ii) a circulator optically connected to the light source by a fiber optic wire;

iii) a polarization controller, wherein a first proximal polarization-maintaining fiber optic wire optically connects the polarization controller to the circulator;

iv) a polarization beam splitter, wherein a second proximal polarization-maintaining fiber optic wire optically connects the polarization beam splitter to the circulator opposite the polarization controller; and v) a reflected light receiver optically connected to the polarization beam splitter opposite the circulator by a third proximal polarization-maintaining fiber optic wire and a fourth proximal polarization-maintaining fiber optic wire; and b) a distal assembly, comprising:

i) a guidewire; and ii) a distal polarization-maintaining fiber optic wire supported by the guidewire, wherein the distal polarization-maintaining fiber optic wire has at least one fiber Bragg grating (FBG) pressure sensing station that is exposable to environment pressure adjacent thereto; and c) an optical connector positioned between the proximal assembly and the distal assembly, the optical connector comprising:

i) a proximal housing containing a proximal single-mode fiber optic wire, the proximal single-mode fiber optic wire extending from a proximal single-mode fiber optic wire proximal end to a proximal single-mode fiber optic wire distal end, wherein the proximal end of the proximal single-mode fiber optic wire is optically connected to the polarization controller opposite the circulator; and ii) a distal housing that is removably mateable with the proximal housing and contains a distal single-mode fiber optic wire, the distal single-mode fiber optic wire extending from a distal single-mode fiber optic wire proximal end to a distal single-mode fiber optic wire distal end, iii) wherein a proximal end of the distal polarization-maintaining fiber optic wire supported by the guidewire is contained in the distal housing optically connected to the distal end of the distal single-mode fiber optic wire, and iv) wherein, when the distal housing is mated with the proximal housing, the proximal end of the distal single-mode fiber optic wire contained in the distal housing is optically connected to the distal end of the proximal single-mode fiber optic wire contained in the proximal housing, and d) wherein, when the guidewire is introduced into the vasculature of a patient, the light source is configured to transmit light along the fiber optic wire to the circulator optically connected to the polarization controller by the first proximal polarization-maintaining fiber optic wire and in turn to the proximal single-mode fiber optic wire, the distal single-mode fiber optic wire and the distal polarization-maintaining fiber optic wire to the at least one fiber Bragg grating (FBG) pressure sensing station, and e) wherein the at least one FBG pressure sensing station is configured to transduce a detected pressure into a reflected wavelength change that is optically transmittable as a polarized light along the distal polarization-maintaining fiber optic wire, the distal single-mode fiber optic wire, the proximal single-mode fiber optic wire optically connected to the polarization controller and then to the circulator by the first proximal polarization-maintaining fiber optic wire and in turn to the polarization beam splitter by the second proximal polarization-maintaining fiber optic wire, the polarization beam splitter serving to split the reflected light into its two polarizations that are optically transmitted to the reflected light receiver by the respective third and fourth polarization-maintaining fiber optic wires, the reflected light receiver being configured to detect the reflected wavelength change for each polarization to thereby determine a pressure value in the vasculature of the patient.

\* \* \* \* \*

UNITED STATES PATENT AND TRADEMARK OFFICE
CERTIFICATE OF CORRECTION

PATENT NO. : 10,548,489 B2  
APPLICATION NO. : 15/129432  
DATED : February 4, 2020  
INVENTOR(S) : John Hayes, Matheus Maria van Leest and Michael Benjamin Haverdings Page 1 of 1

It is certified that error appears in the above-identified patent and that said Letters Patent is hereby corrected as shown below:

In the Specification

Column 6, Line 32, before the letters "FBG", delete the phrase "u-phase-shifted" and insert the phrase --π-phase-shifted--

Column 6, Line 32, after the word "as", delete the phrase "u-phase-shifted" and insert the phrase --π-phase-shifted--

Column 6, Line 35, before the letters "FBG", delete the phrase "u-phase-shifted" and insert the phrase --π-phase-shifted--

Signed and Sealed this  
Ninth Day of March, 2021

Drew Hirshfeld  
*Performing the Functions and Duties of the*  
*Under Secretary of Commerce for Intellectual Property and*  
*Director of the United States Patent and Trademark Office*